(12) United States Patent
Tolliver et al.

(10) Patent No.: US 9,970,866 B1
(45) Date of Patent: May 15, 2018

(54) LASER DETECTOR FOR WEAPONS

(71) Applicants: Charlie Louis Tolliver, Katy, TX (US);
Justin Forman, Spring, TX (US);
Nathaniel Tolliver, II, Woodland Hill, CA (US)

(72) Inventors: Charlie Louis Tolliver, Katy, TX (US);
Justin Forman, Spring, TX (US);
Nathaniel Tolliver, II, Woodland Hill, CA (US)

( * ) Notice: Subject to any disclaimer, the term of this patent is extended or adjusted under 35 U.S.C. 154(b) by 0 days. days.

(21) Appl. No.: 15/655,876

(22) Filed: Jul. 20, 2017

(51) Int. Cl.
*G01N 21/35* (2014.01)
*G01N 21/27* (2006.01)
*G01N 21/3581* (2014.01)
*G01N 21/3563* (2014.01)
*G01N 21/17* (2006.01)

(52) U.S. Cl.
CPC ....... *G01N 21/3581* (2013.01); *G01N 21/274* (2013.01); *G01N 21/3563* (2013.01); *G01N 2021/1793* (2013.01); *G02F 2203/13* (2013.01); *H01S 2302/02* (2013.01)

(58) Field of Classification Search
CPC ............ G01N 21/274; G01N 21/3563; G01N 21/3581; G01N 2021/1793; G02F 2203/13; H01S 2302/02
See application file for complete search history.

(56) References Cited

U.S. PATENT DOCUMENTS

| 2010/0314545 | A1* | 12/2010 | Logan, Jr. ................. G01J 3/10 250/339.07 |
| 2012/0326039 | A1* | 12/2012 | Demers .................... G01J 3/10 250/338.4 |

\* cited by examiner

*Primary Examiner* — Mark R Gaworecki
(74) *Attorney, Agent, or Firm* — Harish Dhingra; Delphine M. James; John R. Casperson

(57) ABSTRACT

A Terahertz laser system for remote weapon detection is disclosed. The human target potentially having a weapon is swept with multiple wavelengths of Terahertz laser beams and the reflected return radiation is detected and transformed into a composite image gradated by brightness or color to represent gradations in intensity of the returned radiation indicative of possible weapon(s) or the absence thereof.

12 Claims, 2 Drawing Sheets

LASER DETECTOR FOR WEAPONS

FIELD OF THE INVENTION

The invention relates to the use of a Terahertz laser system to remotely detect guns and other weapons on persons.

BACKGROUND OF THE INVENTION

Terahertz (THz) lasers produce light of frequency in the range of 0.3 to 4 Terahertz with wave lengths in the range of 75 µm to 1000 µm and are useful at power ranges from 0.02 to 2 watts. These lasers reflect from metals and some organic molecules and are absorbed by water and some polar molecules. The light transmits through clothing, paper, and packaging materials including plastic and cardboard with varying degrees of efficacy depending on wavelength.

The reflectivity from metals and certain explosives, low power and ability to penetrate clothing makes Terahertz lasers a good candidate for remote sensing of weapons on people but heretofore no one has succeeded in producing a device that is effective and compact.

OBJECTS OF THE INVENTION

It is an object of this invention to provide a noninvasive body scanner system that employs a Terahertz laser and detector system to remotely detect weapons.

SUMMARY OF THE INVENTION

One embodiment of the invention comprises a laser source, a detector array, a pitch and yaw mechanism, a computer memory, a display device, and a processor. The laser source emits at least a first laser beam having a first frequency and a second laser beam having a second frequency, each frequency being in the range of from about 0.3 to 4 Terahertz. The detector array is for detecting returned radiation at the first frequency and the second frequency reflected from a portion of a target illuminated by the first laser beam and the second laser beam and producing at least a first electronic signal representative of a characteristic of the detected radiation.

The pitch and yaw mechanism is operatively associated with at least the laser source and optionally with the detector array to sweep at least an area of interest of the target with the at least first laser beam and second laser beam in a sweep pattern and produce a second electronic signal representative of an illumination location in the sweep pattern.

The computer memory is for recording information representative of the first electronic signal in association with the second electronic signal. The display device is for displaying an image representative of returned radiation from within the sweep pattern. The processor is for receiving signals from the computer memory representative of the recorded information and transmitting signals to the display device to form the image representative of the returned radiation.

DETAILED DESCRIPTION OF THE INVENTION

An element of the invention is a Terahertz (THz) laser source. Lasers operating in the Terahertz (THz) range can produce a beam that is non-ionizing with energy levels orders of magnitude less than x-rays, making them safe for human exposure.

There are several suitable THz laser sources, but a preferred source comprises a quantum cascaded laser (QCL) due to its small size, low power requirements, and tunability. A QCL is similar in size to a semiconductor diode laser, which is used for laser pointers, for example. They can be operated at voltages that do not exceed 20 volts, which makes them powerable by ordinary small batteries and capable of being housed in a handheld device. Because they are tunable, a single laser can be used to replace multiple lasers in a multiple wavelength detector system. Furthermore, a QCL has a high signal to noise ratio, up to the order of 100,000 to 1.

Figure 1:
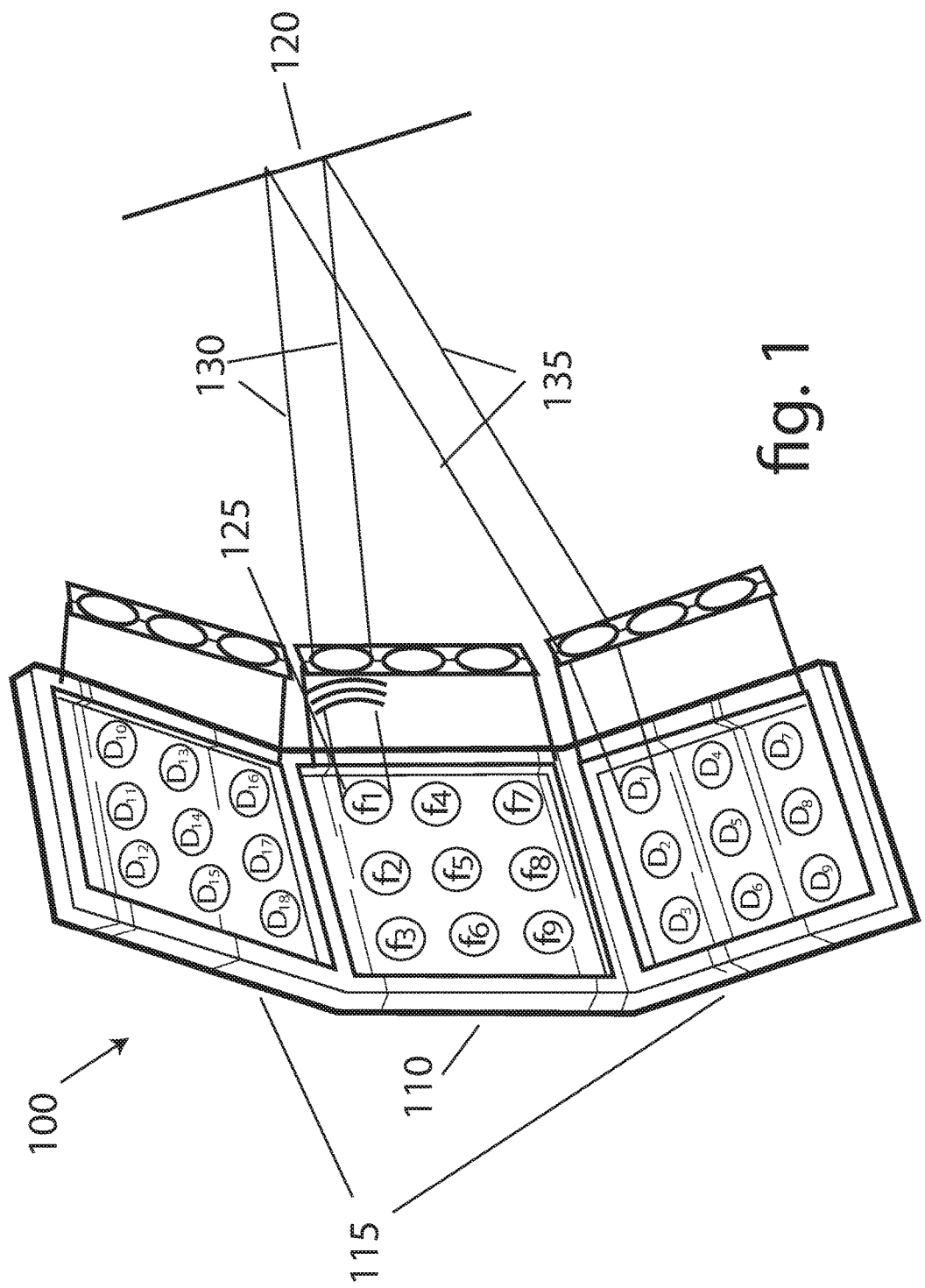
FIG. 1 schematically shows a laser scanning and detection system.
Figure 2:
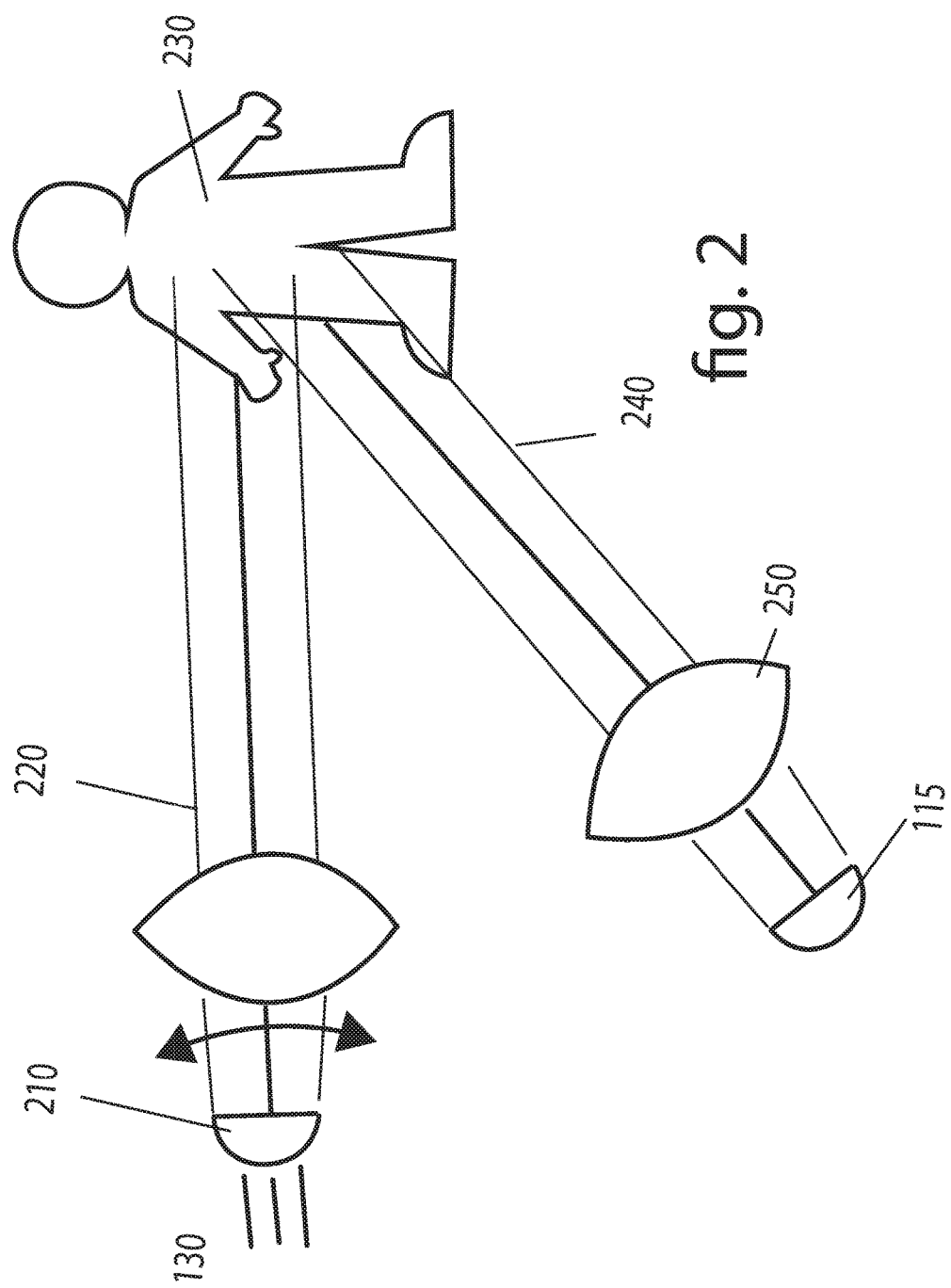
FIG. 2 schematically shows setup for interrogating a target by the laser scanning and detection system.

In FIG. 1, one embodiment 100 of the scanning and detection system of the invention, shows a rectangular array 110 of QCLs is positioned to emit beams 130 toward a target 120 from a scanner/detector device. Each QCL 125 is tuned to emit light of a different frequency. Also referring to FIG. 2, the beams 130 are diffracted by passing through an aperture 210, and then are collimated to form a large diameter spreading beam 220 that is directed toward the human target 230. At a distance of 10 in, an exemplary beam can have a diameter of about 10 cm.

The frequencies of the beams are selected from Terahertz wavelengths that have good propagation through air at various humidities. Windows of good propagation exist near 0.350, 0.6, 0.8, 1.5, 2, 2.1, 2.53, and 3.4 Terahertz. Beams at each frequency react differently to encountered targets. That is why it is important to scan the target with multiple beams at multiple frequencies, at least some of which are preferably selected from the aforementioned windows.

The human targets comprise skin, hair, clothing, possible hard objects such as concealed weapons, and possible chemical objects such as explosives. The incident beam produces a reflected signal back to the scanner/detector device 115 at an intensity that is dependent on several factors, including the reflectivity of the target encountered to the particular wavelength of the incident beam and the shape of the object. The reflected beam is passed through a lens 250 to focus it sufficiently for detection by a detector. A heterodyne detector array can be employed to detect the reflected beam.

The system is illustrated in the FIG. 1 for a single laser in the laser array and a single detector in the detector array.

To interrogate a human target, the device is pointed at them and a first laser beam actuated. The reflected first beam is detected by the device and electronically recorded. The laser source is re-aimed or scanned over to an adjacent area with a pitch and yaw mechanism (not shown), and the reflection recorded, and the process is repeated until the target has been adequately, generally completely, interrogated with the first laser beam. The process is then repeated with the second laser beam, then, if used, the third laser beam, etc. until the target has been interrogated with all available beams. The recorded reflections then merged to form and display a composite raster image of the target identifying any hard reflections at one or more frequencies that may be indicative of an undesirable object such as a weapon.

Alternatively, the device can be pointed at an area of the human target, the first laser beam actuated and the image recorded. The process is then automatically repeated for the second, third, fourth, etc. laser beams, very quickly and a first composite reflection value formed for the area such as by combining and mixing the reflected THz waves with an oscillator. The composite reflection value is stored in association with an area of the target. The array would then be automatically re-aimed at an adjacent area of the target using the pitch and yaw mechanism operatively associated (mechanical, electro-mechanical, and/or electronic) with the rectangular arrays and the process repeated to produce a second composite reflection value associated with a second area of the target. The re-aiming and production of composite reflection values associated with an area of the target is continued until the target has been adequately, generally completely, interrogated. The recorded reflections are then merged to form a composite raster image of the target identifying any hard reflections at one or more frequencies that may be indicative of a weapon. For example, in one embodiment the strongest intensity signal, reflected from a region is selected in forming the image which otherwise may escape detection/identification of the object.

As a third option, the target can be scanned with all available beams aimed at the same area at once. The return reflections are detected by different detectors tuned to the wavelengths of the different outgoing lasers, or the oscillators of the detectors are stepped through a tuning sequence to sample the reflected radiation. Composite reflection values are formed and associated with areas of the target in computer memory, and the array is automatically re-aimed using the pitch and yaw mechanism to interrogate the entire target. The recorded reflections then merged to form a composite raster image of the target identifying any hard reflections at one or more frequencies that may be indicative of a weapon.

If the return signal is insufficient to process data, the device could issue a signal or message to indicate that the target must be interrogated at a closer range. If a return signal indicates a hard reflection, the device could immediately issue a signal or message that a possible hard weapon or RDX explosive is associated with the target. If the return signal shows an area of signal absorbance, the device could immediately issue a signal or message that a possible non-RDX explosive device is associated with the target.

It is ordinarily not necessary to produce an image allowing the identification of weapons. For a hand held device, a determination that the target is either clean or suspicious is generally adequate for appropriate follow-up by appropriate personnel. For a stationary device or machine-aimed device, suspicious areas of the target can be re-interrogated to obtain greater resolution.

The system can be stationary, vehicle-mounted, or carried by human, drone, or remotely operated terrestrial vehicle.

While certain preferred embodiments have been described herein, the invention is not to be construed as being so limited, except to the extent that such limitations are found in the claims.

What is claimed is:

1. An apparatus comprising a laser source for emitting at least a first laser beam having a first frequency and a second laser beam having a second frequency, each frequency being in the range of 0.3 to 4 Terahertz,
   a detector array for detecting returned radiation reflected from a portion of a target illuminated by the at least first and second laser beams and producing a first electronic signal representative of a characteristic of the detected radiation,
   a pitch and yaw mechanism operatively associated with at least the laser source and optionally with the detector array to sweep at least an area of interest of the target with the at least first and second laser beams in a sweep pattern and produce a second electronic signal representative of an illumination location in the sweep pattern,
   a computer memory for recording information representative of the first electronic signal in association with the second electronic signal,
   a display device for displaying an image representative of returned radiation from within the sweep pattern, and
   a processor for receiving signals from the computer memory representative of the recorded information and transmitting signals to the display device to form the image representative of the returned radiation.

2. An apparatus as in claim 1 wherein the laser source is at least one quantum cascaded laser and at least one of the laser beams has a frequency selected from near 0.35, 0.6, 0.8, 1.5, 2.0, 2.1, 2.53, or 3.4 Terahertz.

3. An apparatus as in claim 2 wherein the laser source includes an aperture for diffracting the laser beam and a collimator for collimating the diffracted laser beam.

4. Apparatus as in claim 2 wherein the laser source comprises a single quantum cascaded laser and a tuner to cause the quantum cascaded laser to produce the first laser beam and the second laser beam.

5. Apparatus as in claim 4 wherein the tuner produces laser beam frequencies selected from near 0.35, 0.6, 0.8, 1.5, 2.0, 2.1, 2.53, and 3.4 Terahertz.

6. An apparatus as in claim 1 wherein the detector array includes a plurality of heterodyne detectors each including an oscillator and a photodiode for producing the first electronic signals.

7. An apparatus as in claim 6 wherein each detector array includes a focuser for each heterodyne detector to concentrate the returned radiation for processing by its respective heterodyne detector.

8. Apparatus as in claim 6 wherein the area of interest is swept simultaneously with the first laser beam and the second laser beam and a first portion of the plurality of heterodyne detectors includes an oscillator and a photodiode tuned for reflections from the first laser beam and a second portion of the heterodyne detectors includes an oscillator and photodiode tuned for reflections from the second laser beam.

9. Apparatus as in claim 6 wherein the area of interest is swept simultaneously with the first laser beam and the second laser beam and the oscillators of the detectors are stepped through a tuning sequence to sample the reflected radiation from each beam.

10. An apparatus as in claim 1 wherein the processor operates in conjunction with the display device to produce a rasterized image of the target gradated by brightness or color to represent gradations in intensity of the returned radiation.

11. Apparatus as in claim 1 wherein the area of interest of the target is swept by the first laser beam and then by the second laser beam.

12. Apparatus as in claim 11 wherein the pitch and yaw mechanism is operatively associated with both the laser array and the detector array.

* * * * *